United States Patent
Sorensen

[19]

[11] Patent Number: 6,159,007
[45] Date of Patent: Dec. 12, 2000

[54] AUTOCLAVEABLE DENTAL UNIT WATER LINE AND PRE-FILTER

[76] Inventor: Jerold R. Sorensen, 1480 W. Herndon Ave., Fresno, Calif. 93711

[21] Appl. No.: 09/270,126

[22] Filed: Mar. 15, 1999

[51] Int. Cl.⁷ ...................................................... A61C 1/10
[52] U.S. Cl. .............................. 433/80; 433/82; 210/651; 210/321.64
[58] Field of Search ................................. 433/80, 81, 82, 433/83, 84, 85, 86, 87, 89; 210/321.64, 651, 321.72, 321.75, 321.84, 321.6

[56] References Cited

U.S. PATENT DOCUMENTS

| | | | |
|---|---|---|---|
| 4,950,159 | 8/1990 | Hansen | 433/80 |
| 5,204,004 | 4/1993 | Johnston et al. | 210/651 |
| 5,370,534 | 12/1994 | Wolf et al. | 433/80 |
| 5,554,025 | 9/1996 | Kinsel | 433/80 |
| 5,709,545 | 1/1998 | Johnston et al. | 433/80 |
| 5,764,835 | 6/1998 | Rubin et al. | 385/104 |

*Primary Examiner*—Pedro Philogene
*Attorney, Agent, or Firm*—Richard A. Ryan

[57] ABSTRACT

A detachable autoclaveable dental unit water line and pre-filter having a water line made of a thermoplastic fluoropolymer tubing that connects to standard dental handset or tools. The fluoropolymer tubing is suitable for sterilization in the typical autoclave units that are used in dental facilities due to the tubing's ability to withstand the high temperatures used in the autoclave. Use of the autoclave facilitates sterilization of active biofilm, which biofilm provides a mechanism for the growth and distribution of bacteria, that has a tendency to accumulate in the water line tubing. The pre-filter is connected at the opposite end of the fluoropolymer tubing from the dental handset or tool and is releasably connected to the water supply to filter out bacteria and other materials in the water supply to prevent recolonization of the biofilm.

14 Claims, 1 Drawing Sheet

AUTOCLAVEABLE DENTAL UNIT WATER LINE AND PRE-FILTER

BACKGROUND OF THE INVENTION

1. Field of the Invention

The field of the present invention relates generally to devices and methods which prevent, inhibit or impede the build-up of bacteria in water lines which connect dental or medical tools to a source of water. More particularly, the present invention relates to sterilizable water lines and pre-filters that connect dental handset tools (air/water syringe dental handpiece, or ultrasonic scaling device) to a supply of water to prevent bacteria from passing through the tool to the patient.

2. Background

In recent years, much media concern and in some cases criticism has been focused on the equipment and processes utilized by dental personnel regarding the transmission of microorganisms during dental procedures. Much of this attention has been focused on unsterilized fluids being introduced into a patient's mouth and exposed tissues. These microorganisms may result in harmful illnesses that are difficult to treat. As more progress and knowledge is gained regarding this problem, modern dental practices attempt to reduce the potential for transmission of microorganisms. However, the very nature of many dental procedures, which continue to be somewhat invasive, and the current state of technology makes this task difficult to completely resolve.

One source of potential concern is the water that is injected into the patient's mouth during a number of different dental and oral surgical procedures. For instance, water is used to rinse off scale and tartar debris that is released from ultrasonic scaling and cleaning procedures. The injection of water allows the dental personnel to better determine which areas need cleaning and allows the patient to remove the debris from the mouth. The use of high-speed dental tools for drilling and grinding, which can generate significant heat, are made somewhat less painful by the injection of a small stream of water to cool the tools. Water is also used to remove debris from the drilling. Other specialized equipment also requires the injection of water and air/water spray into the patien's mouth. When used with dental water syringes, the water is commonly supplied into the patien's mouth at a pressure of about ±40 psi.

The source of water for most dental offices is city tap water that is conveyed through a dental unit workstation to thermoplastic tubing connected to the dental tools. Often these workstations do not employ filtering systems to filter bacteria and other contaminants from the water source, as there is no legal standard to require this at present. Despite this, recent national media attention and criticism has focused on the problems with city water that is injected into the patien's mouth. According to published reports, the city water or other water entering the dental tools is often contaminated with significant levels of various microorganisms. Also, water left in the water lines incubates and forms a biofilm which increases the bio-burden that is injected into patients' mouth. Because many dental procedures are invasive and result in some bleeding in the patien's mouth, it is possible for this bacteria to enter the person's blood stream and, possibly, result in illness for the patient. This is a particular concern for those patients with weakened immune systems, the very young, the elderly and those who are already ill.

Much progress has occurred relative to the sterilization of dental tools to prevent the tools, themselves, from being a source of contaminate transmission. In recent years, OSHA and others have set guidelines that require dental tools to be sterilized on a routine basis. The typical sterilization procedure used in dental offices is to place the dental tools to be sterilized in an autoclave for approximately 30 minutes. The autoclave is a self-contained unit that heats the dental tools to an elevated temperature of approximately 132 degrees C. (270 degrees F.) at a pressure of approximately 15 psi. This procedure has been found to be very effective for eliminating the patient to patient cross contamination and transmission of bacteria by the dental tools, which are typically manufactured out of stainless steel and similar autoclaveable materials. However, the high temperatures in the autoclave are known to deteriorate the materials used for existing water lines and, consequently, the autoclave has not been used to sterilize water lines due to their fragility. Also, water lines heretofore have not been detachable for the purpose of sterilization.

Research by others have indicated that the small bore water lines utilized in the dental profession have a tendency to accumulate a layer of biofilm, consisting of a form a mucopolysaccharide slime and microorganisms, on the inside of the water line. This biofilm is formed when water sits in the water line at room temperature for hours without circulation, allowing bacteria in the lines to multiply in the biofilm and adhere to the walls of the water line. Once established, the biofilm cannot easily be removed by conventional cleaning. The bacteria in the biofilm are shed from the biofilm into the water that is injected into the patien's mouth. While most dental tools and equipment can be effectively sterilized by the use of autoclave systems, the biofilm in the water lines is upstream of the dental tool and not included in such cleaning of the dental tools. Also the water lines are susceptible to deterioration by heat and therefore not autoclaved. Prior art dental water lines have one or more small bores, and they are typically molded from a thermoplastic or plastic-composite material. The high temperature inside the autoclave can damage or even melt these prior art water lines, making the autoclave ineffective for sterilization. Because the biofilm attaches itself to the inside of the line and tends to become entrenched in the line, it is difficult to remove by other sterilization procedures (i.e., chemical processes). In addition to being difficult to remove, if the biofilm is removed by a particular cleaning process, it tends to quickly and easily re-establish itself in the water line, thereby requiring frequent re-cleaning of the water line.

Several previous inventions have attempted to address the problem of biofilm accumulation in water lines. For instance, U.S. Pat. No. 5,204,004 to Johnson, et al. and U.S. Pat. No. 5,554,025 to Kinsel have both addressed the problem of biofilm accumulation in dental water lines. Both Johnson and Kinsel disclose filters that are intended to filter out contaminants after the line but before they are injected into the patien's mouth (i.e. at the dental handpiece). Johnson places a post water line filter on the water line a small distance before the dental syringe. Kinsel utilizes a filter located between the syringe tip and the dental handset outlet fitting. Choosing to rely on filters, neither Johnson or Kinsel address the accumulation or removal of biofilm in the water line between the filter and the dental tool. However short that this line may be, it still continues to grow biofilm. Therefore, what is needed is a method and/or detachable device to prevent, control or reduce the accumulation of biofilm in the water line and to reduce its bio-activity by use of commonly available sterilization methods, such as autoclaving.

SUMMARY OF THE INVENTION

The autoclaveable and detachable water line in accordance with the present invention solves the problems identified with the current water lines described above. That is to say, the present invention provides a water line that is detachable and suitable for sterilization in a autoclave to eliminate bioactivity of the biofilm and, as a result, bacteria accumulation without violating the integrity of the water line. The detachable water line of the present invention is made of a material that has a sufficiently high melting temperature that it can withstand repeated autoclaving without damage. Because the water line can be autoclaved, it can be sterilized as frequently as other dental tools to prevent the entrenchment of the biofilm in the water line. An autoclaveable pre-filter used with the water line of the present invention prevents the re-introduction of contaminates from the city water supply.

The present invention provides an autoclaveable dental water line that is made of a nonporous thermoplastic fluoropolymer material that is injection molded into a dental unit water line having one or more passageways (e.g., it is not unusual to have five passageways or bores). An autoclaveable, detachable pre-filter is used in conjunction with the water line to prevent re-contamination from any water supply between sterilization of the water line. The fluoropolymer water line can withstand repeated exposure to the high temperatures used in autoclaves without deterioration of the water line. The housing for the detachable pre-filter is also made of an autoclaveable material, preferably a machinable Delrin material, so that it can be sterilized in the autoclave with the water line. One end of the filter housing connects directly to the dental water line. The other end of the filter housing is provided with a quick release mechanism for easy connection and removal from the city and other water supply. A replaceable disposable filter disc with a pore size of 0.2 microns inside the filter housing should be suitable for filtering out contaminants that flow through the tubing from the city and other water supply between autoclaving of the tubing.

Accordingly, the primary objective of the present invention is to provide detachable, autoclaveable water line for use in dental and other like uses to eliminate bioactive biofilm and prevent recontamination.

It is also an important objective of the present invention to provide an autoclaveable water line having a pre-filter attachable to one end of the water line between the water line and the water supply.

It is also an important objective of the present invention to provide quick connect, detachable, autoclaveable dental unit water line and an autoclaveable pre-filter housing made of a thermoplastic fluoropolymer material.

It is also an objective of the present invention to provide a method for supplying water to a dental tool through a water line that can be maintained relatively free of bacteria laden biofilm.

The above and other objectives of the present invention will be explained in greater detail by reference to the attached figures and the description of the preferred embodiment which follows. As set forth herein, the present invention resides in the novel and unique features of form, construction, mode of operation and combination of parts presently described and understood by the claims.

BRIEF DESCRIPTION OF THE DRAWINGS

In the drawings which illustrate the best modes presently contemplated for carrying out the present invention.

DETAILED DESCRIPTION OF THE PREFERRED EMBODIMENTS

Figure 1:
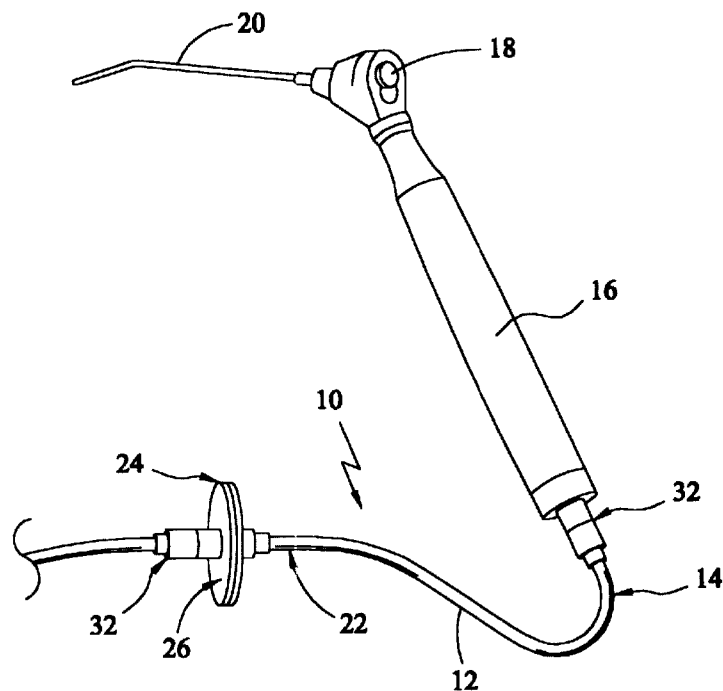
FIG. 1 is a perspective view of the detachable, autoclaveable dental unit water line and autoclaveable pre-filter of the present invention.
Figure 2:
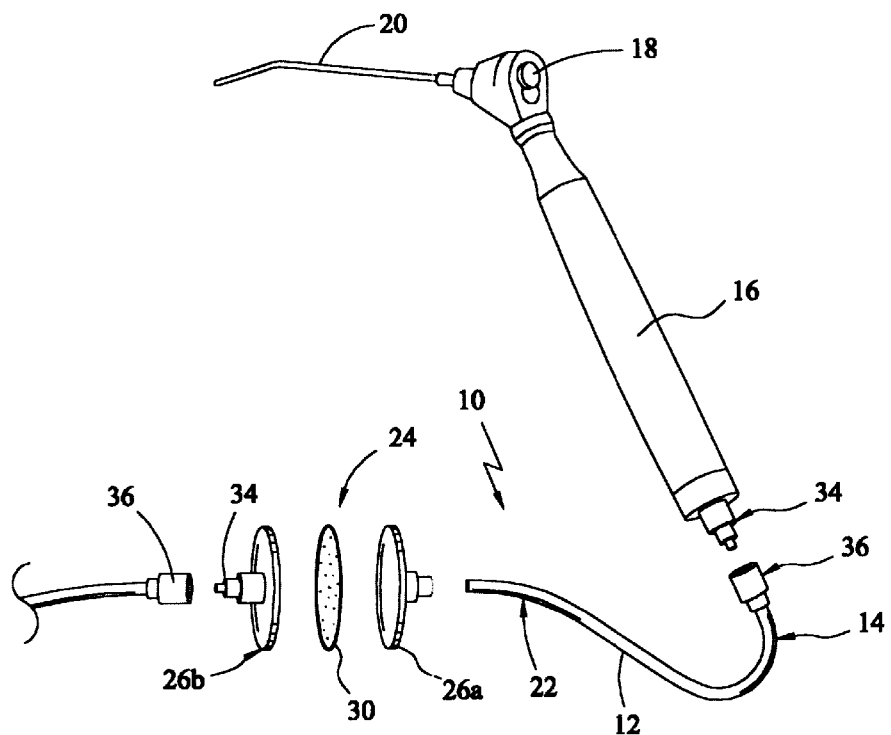
FIG. 2 is an exploded view of the embodiment illustrated in FIG. 1.

With reference to FIGS. 1 and 2 where like elements have been given like numerical designations to facilitate the reader's understanding of the present invention, the preferred embodiment of the present invention is set forth below. The autoclaveable, detachable water line of the present invention, designated generally as 10, includes a tubular water line 12 made of a thermoplastic fluoropolymer material having properties that allow it to be autoclaved without damage to the tubing. Fluoropolymers are characterized by the fact that they are highly inert, paraffinic thermoplastic extrudeable polymers that have all or some of all of the hydrogen replaced with fluorine. Nonporous Fluoropolymer materials include such materials as polytetrafluoroethylene (PTFE), fluorinated ethylene propylene (FEP), and perfluoroalkoxytetrafluoroethylene (PFA), which are all capable of being extruded, stretched and formed into a tubular shape suitable for use as a dental unit water line.

The first end 14 of tubing 12 is configured to be detachable and quick connect (as explained below) to dental tools, such as dental handset 16 (i.e., an air/water syringe, dental handpiece/drill or ultrasonic scaling device). As shown in FIG. 1, the typical dental handset 16 has control button 18 to control the flow of water from tubing 12 through syringe tip 20 into the patien's mouth. The opposite end 22 of tubing 12 connects to pre-filter 24 for filtering out contaminates, such as bacteria, that are known to exist in the typical municipal or other water supply system. Pre-filter 24 and tubing 12 can be provided as a single piece, both made from the same fluoropolymer material, or as a separate component. For example, pre-filter 24 can be one of a number of readily available filters, such as those filters made of DELRIN (a registered trademark of E.I. du Pont de Nemours & Co.) that are suitable for autoclaving. As shown best in FIG. 2, pre-filter 24 is made up of housing body 26 having two or more separatable housing members 26a and 26b, which can have an O-ring or the like to seal the two housing members 26a and 26b together to enclose a disposable, replaceable filter member 30. Because housing body 26 is made of an autoclaveable material, housing body 26 can be autoclaved with tubing 12. Housing members 26a and 26b separate to allow the user to remove and replace the filter member 30 on a regular basis. Filter member 30 is sized and configured to fit within housing body 26 and filter out bacteria and other material found in the water supply. Filter member 30 should provide the dental personnel a relatively unrestricted high flow rate of water through dental unit 16. For this purpose, filter members 30 having 0.2 micron pore size have been found to be able to filter out bacteria yet provide a relatively unrestricted rate of fluid flow.

The opposite side of housing body 26 should comprise a quick release mechanism, such as the quick release coupling mechanism 32 of FIG. 1, shown best in FIG. 2. The use of coupling mechanism 32, comprising of a male member 34 connected to housing member 26b and female member 36 connected to the water supply, facilitates removal of the pre-filter 24 and tubing 12 from the water supply for autoclaving. Naturally, some systems will have the male member 34 and female member 36 reversed. This same quick release mechanism can be utilized at first end 14 of tubing 12.

In use, the first end 14 of sterilized tubing 12 is quick connected to the dental handset 16, which can be operated to inject water into the patien's mouth. The second end 22 of tubing 12 is connected to pre-filter 24. Pre-filter 24 is connected to the water supply by connecting male member 34 to female member 36 that is connected to the water supply. A new filter member 30 is placed inside filter housing 26. Water supply is initiated to flow water through tubing 12 to handset 16 for use in dental procedures.

For cleaning, the first end 14 of tubing 12 is removed from the handset 16 and the male member 34 is disconnected from the female member 36. Filter member 30 is removed from filter housing 26 and the entire unit 10 is placed in an autoclave for sterilization. If pre-filter 24 separates from tubing 12, the second end 22 of tubing 12 is separated from housing member 26a and the separate pieces are placed in the autoclave for sterilization. After sterilization, a new filter member 30 is placed within filter housing 26 to filter incoming water and prevent re-colonization of the biofilm.

While there is shown and described herein certain specific alternative forms of the invention, it will be readily apparent to those skilled in the art that the invention is not so limited, but is susceptible to various modifications and rearrangements in design and materials without departing from the spirit and scope of the invention. In particular, it should be noted that the present invention is subject to modification with regard to the dimensional relationships set forth herein and modifications in assembly, materials, size, shape and use.

What is claimed is:

1. A detachable autocleaveable water line, comprising a length of tubing, said tubing having a first end and a second end, said tubing manufactured of a thermoplastic fluoropolymer material suitable for sterilization in an autoclave to remove biofilm contamination or prevent biofilm build-up, said first end of said tubing configured for connection to a dental tool, said second end of said tubing configured for connection to a supply of water.

2. The detachable, autoclaveable water line of claim 1 further comprising a quick release means interconnecting said second end of said tubing and said water supply for releasably connecting said second end of said tubing to said supply of water.

3. The detachable, autoclaveable water line of claim 1 further comprising a quick release means interconnecting said first end of said tubing and said dental tool for releasably connecting said first end of said tubing to said dental tool.

4. The detachable, autoclaveable water line of claim 1 further comprising a filter means disposed between said second end of said tubing and said supply of water for filtering water from said supply of water.

5. The detachable, autoclaveable water line of claim 4, wherein said filter means comprises a filter housing and a filter member within said filter housing.

6. The detachable, autoclaveable water line of claim 5, wherein said filter member is removable from said filter housing.

7. A detachable, autoclaveable water line, comprising:
  a length of tubing, said tubing having a first end and a second end, said tubing manufactured of a fluoropolymer material suitable for sterilization in an autoclave to remove biofilm contamination or prevent biofilm build-up, said first end of said tubing configured for connection to dental handset or tool, said second end of said tubing configured for connection to a supply of water;
  a quick release means interconnecting said second end of said tubing and said water supply for releasably connecting said second end of said tubing to said supply of water; and
  a filter means disposed between said second end of said tubing and said supply of water for filtering water from said supply of water.

8. The detachable, autoclaveable water line of claim 7 further comprising a quick release means interconnecting said first end of said tubing and said dental tool for releasably connecting said first end of said tubing to said dental tool.

9. The detachable, autoclaveable water line of claim 7, wherein said filter means comprises a filter housing and a filter member within said filter housing.

10. The detachable, autoclaveable water line of claim 9, wherein said filter member is removable from said filter housing.

11. The method of supplying water to a dental tool through a length of fluropolymer tubing suitable for sterilization in an autoclave to remove biofilm contamination or prevent biofilm build-up, comprising the following steps:
  a) attaching a first end of said length of fluoropolymer tubing to said dental handset or tool;
  b) attaching a second end of said length of fluoropolymer tubing to a supply of water; and
  c) initiating a flow if water from said supply of water through said length of fluoropolymer tubing to said dental handset or tool.

12. The method of supplying water to a dental handset or tool through a length of fluoropolymer tubing of claim 11, wherein said length of fluoropolymer tubing includes a filter means disposed between said water supply and said dental handset or tool.

13. The method of supplying water to a dental handset or tool through a length of fluoropolymer tubing of claim 12, wherein said filter means is connected to said length of fluoropolymer tubing with a releasable connection means.

14. The method of supplying water to a dental handset or tool through a length of fluoropolymer tubing of claim 11, further comprising the steps of:
  d) disconnecting said first end of said length of fluoropolymer tubing from said dental handset or tool and said second end of said length of fluoropolymer tubing from said supply of water; and
  e) placing said length of fluoropolymer tubing in an autoclave to sterilize said length of fluoropolymer tubing to remove bacteria and prevent biofilm build-up.

\* \* \* \* \*